United States Patent [19]

Barthelemy et al.

[11] Patent Number: 5,623,150

[45] Date of Patent: Apr. 22, 1997

[54] PROCESS FOR THE STABILIZATION OF COMPOSITIONS CONTAINING HYDROFLUOROALKANES AND STABILIZED COMPOSITIONS CONTAINING HYDROFLUOROALKANES

[75] Inventors: Pierre Barthelemy, Jodoigne, Belgium; Lothar Zipfel, Laatzen; Thomas Benecke, Hannover, both of Germany

[73] Assignee: Solvay (Société Anonyme), Brussels, Belgium

[21] Appl. No.: 266,535

[22] Filed: Jun. 27, 1994

Related U.S. Application Data

[62] Division of Ser. No. 16,216, Feb. 11, 1993, abandoned.

[30] Foreign Application Priority Data

Feb. 14, 1992 [BE] Belgium ............................. 09200161

[51] Int. Cl.$^6$ ..................................................... C09K 3/00
[52] U.S. Cl. ....................................................... 252/182.24
[58] Field of Search ........................ 570/102; 252/182.24

[56] References Cited

U.S. PATENT DOCUMENTS 4,475,003 10/1984 Fischer .
5,366,946 11/1994 Barthelemy .

FOREIGN PATENT DOCUMENTS 0503441 9/1992 European Pat. Off. .
1375697 9/1964 France .
4107245 9/1992 Germany .

OTHER PUBLICATIONS

Chemical Abstracts, vol.81, No. 19, Nov. 11, 1974; Abstract No. 119905m, Takeshi Kawamoto et al., "Stabilization of Chlorinated Hydrocarbons", p. 473.

*Primary Examiner*—Alan Siegel
*Attorney, Agent, or Firm*—Spencer & Frank

[57] ABSTRACT

Process for the stabilization of compositions containing hydrofluoroalkanes by addition of at least one salt of at least one metal chosen from lithium and/or the alkaline-earth metals in a sufficient quantity to stabilize the hydrofluoroalkanes and stabilized compositions containing hydrofluoroalkanes.

8 Claims, No Drawings

PROCESS FOR THE STABILIZATION OF COMPOSITIONS CONTAINING HYDROFLUOROALKANES AND STABILIZED COMPOSITIONS CONTAINING HYDROFLUOROALKANES

This is a division of application Ser. No. 08/016,216 filed Feb. 11, 1993, now abandoned.

The present invention relates to a process for the stabilisation of compositions containing hydrofluoroalkanes as well as stabilised compositions containing hydrofluoroalkanes.

The entirely halogenated chlorofluorinated hydrocarbons (CFC), suspected of having a harmful effect on the ozone layer, can be substituted in many applications, such as, for example, the use as a blowing agent for the preparation of foams, as a liquid coolant or as a propellant, by partially halogenated fluorinated hydrocarbons, also called hydrofluoroalkanes (HFA).

However, the HFA are generally less stable than the CFC, so that their use in the abovementioned fields still poses a problem of stability.

The subject of the present invention is to provide new efficient stabilising agents for hydrofluoroalkanes in the compositions which contain them.

The invention relates to a process for the stabilisation of compositions containing hydrofluoroalkanes, characterised in that there is added thereto at least one salt of at least one metal chosen from lithium and/or the alkaline-earth metals in a sufficient quantity to stabilise the hydrofluoroalkanes contained in the composition.

The term hydrofluoroalkanes is generally intended to denote the saturated halogenated aliphatic hydrocarbons containing at least one fluorine atom and at least one hydrogen atom. These hydrofluoroalkanes may or may not additionally contain one or more chlorine atoms. Preferably, they contain at/least one chlorine atom. The hydrofluoroalkanes as defined generally contain from 1 to 3 carbon atoms. There may be mentioned, as an example of such hydrofluoroalkanes, 1,1-dichloro-1-fluoroethane.

The process according to the invention can be used for the stabilisation of compositions containing one or more hydrofluoroalkanes. Moreover, it can be used for the stabilisation of compositions consisting essentially of one or more hydrofluoroalkanes.

Among the alkaline-earth metals, there are used, in particular, magnesium, calcium, strontium and barium. More particularly, magnesia, calcium or strontium, and preferably magnesium or calcium, is chosen. Excellent results have been obtained with calcium.

The salts used can be organic or inorganic salts. Among the inorganic salts, there may be used, in particular, nitrates or halides. Among the latter, fluorides, bromides or chlorides are more particularly retained. Excellent results have been obtained with chlorides.

Stabilising salts according to the invention can be used in the anhydrous or hydrated form. They are preferably used in the solid state.

The stabilising salts according to the invention can be used at variable doses. They are generally used at a content of at least 0.05% by weight with respect to the total weight of hydrofluoroalkanes contained in the composition. Preferably at least 0.1% of them are used. Moreover, there is not usually used more than 5% by weight of salt of at least one metal chosen from lithium and/or the alkaline-earth metals with respect to the total weight of hydrofluoroalkanes contained in the composition. Preferably, 2% is not exceeded.

Other stabilising agents and/or other additives can also be added to the hydrofluoroalkanes in the stabilised compositions according to the invention.

The present invention also relates to compositions containing hydrofluoroalkanes, characterised in that they contain at least one salt of at least one metal chosen from lithium and/or the alkaline-earth metals in a sufficient quantity to stabilise the hydrofluoroalkanes contained in the composition.

The nature of the stabilising salts and the quantities in which these (are advantageously used, as well as the nature of the compositions containing hydrofluoroalkanes, are those described above in the context of the process according to the invention.

The compositions according to the invention can advantageously be used as blowing agents, as liquid coolants, as propellants or also as solvents.

The compositions according to the invention can, in particular, consist of premixtures, containing hydrofluoroalkanes as blowing agents, intended for the preparation of foams, such as polyurethane foams. These compositions more particularly consist of polyol-based premixtures, containing hydrofluoroalkanes as blowing agents, intended for the manufacture of polyurethane foams. Excellent results have been obtained with compositions consisting of polyol-based premixtures, containing 1,1-dichloro-1-fluoroethane as blowing agent, intended for the manufacture of polyurethane foams. Such compositions can also contain one or more other blowing agents. They have proven to be particularly stable in the presence of calcium chloride, giving rise, in particular, to only a very limited formation of 1-chloro-1-fluoroethane.

The examples which follow are given, in a non-limiting way, in order to illustrate the invention. Example 1 is given as reference.

EXAMPLES

Example 1R (reference)

A premixture for the preparation of polyurethane foams is prepared according to the following composition, by weight:

| | |
|---|---|
| 50 | aminated polyol ARCOL 3770 from Arco |
| 50 | aminated polyol VORANOL RA 640 from Dow |
| 1 | water |
| 2 | silicone-containing surfactant B 1048 from Goldschmidt |
| 2 | N-methylmorpholine |
| 1.5 | N,N-dimethylcyclohexylamine |
| 24 | 1,1-dichloro-1-fluoroethane |

A predetermined quantity of this mixture is confined in a glass flask maintained at a constant temperature of 50° C. for 10 days.

A sample is then withdrawn and its analysis by gas phase chromatography shows the presence of 256 mg of 1-chloro-1-fluoroethane per kg of 1,1-dichloro-1-fluoroethane.

Example 2

There is added to a premixture identical to that of Example 1R, before ageing, 0.5% by weight of anhydrous calcium chloride with respect to the weight of 1,1-dichloro-1-fluoroethane.

After ageing under conditions identical to those of Example 1R, only 29 mg of 1-chloro-1-fluoroethane per kg of 1,1-dichloro-1-fluoroethane are measured by gas phase chromatography.

Example 3

There are added to a premixture identical to that of Example 1R, before ageing, 5% by weight of anhydrous calcium chloride with respect to the weight of 1,1-dichloro-1-fluoroethane.

After ageing under conditions identical to those of Example 1R, the quantity of 1-chloro-1-fluoroethane present is below the detection threshold by gas phase chromatography, which is 5 mg per kg of 1,1-dichloro-1-fluoroethane.

By comparison with reference Example 1R, Examples 2 and 3 show that the quantity of 1-chloro-1-fluoroethane formed is very markedly less and thus the stability of 1,1-dichloro-1-fluoroethane is very substantially improved in the presence of calcium chloride according to the invention.

We claim:

1. In a premixture for the manufacture of a polyurethane foam, the improvement comprising a composition containing at least one hydrofluoroalkane, a polyol, and at least one salt of at least one metal selected from the group consisting of lithium and alkaline-earth metals in an effective amount to stabilise the hydrofluoroalkane.

2. The premixture according to claim 1, wherein said hydrofluoroalkane is 1,1-dichloro-1-fluoroethane.

3. The composition according to claim 1, wherein said salt is calcium chloride.

4. The premixture according to claim 2, wherein said salt is calcium chloride.

5. The premixture according to claim 1, including from 0.5 to 5% by weight of at least one salt of at least one metal selected from the group consisting of lithium and alkaline-earth metals with respect to the total weight of said at least one hydrofluoroalkane.

6. The premixture according to claim 2, including from 0.5 to 5% by weight of said at least one salt of at least one metal selected from the group consisting of lithium and alkaline-earth metals with respect to the total weight of said 1,1-dichloro-1-fluoroethane.

7. The premixture according to claim 1, wherein said at least one salt is selected from the group consisting of organic salts and inorganic nitrates of halides of at least one metal selected from the group consisting of lithium and alkaline-earth metals.

8. The premixture according to claim 2, wherein said at least one salt is selected from the group consisting of organic salts and inorganic nitrates of halides of at least one metal selected from the group consisting of lithium and alkaline-earth metals.

* * * * *